United States Patent
Forghani et al.

(10) Patent No.: US 10,888,658 B2
(45) Date of Patent: Jan. 12, 2021

(54) DISPOSABLE INJECTOR WITH INCREASED TRIGGERING RELIABILITY

(71) Applicant: LTS LOHMANN THERAPIE-SYSTEME AG, Andernach (DE)

(72) Inventors: Sara Forghani, Urbar (DE); Uwe Wortmann, Marburg (DE); Karsten Heuser, Bad Breisig (DE); Heiko Spilgies, Koblenz (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 488 days.

(21) Appl. No.: 15/793,295

(22) Filed: Oct. 25, 2017

(65) Prior Publication Data
US 2018/0056000 A1 Mar. 1, 2018

Related U.S. Application Data

(63) Continuation-in-part of application No. PCT/EP2015/059714, filed on May 4, 2015.

(51) Int. Cl.
*A61M 5/20* (2006.01)
*A61M 5/315* (2006.01)

(52) U.S. Cl.
CPC ........ *A61M 5/2033* (2013.01); *A61M 5/3158* (2013.01); *A61M 2005/2073* (2013.01)

(58) Field of Classification Search
CPC ........ A61M 5/20; A61M 5/2033; A61M 5/30; A61M 5/3007; A61M 5/3015;
(Continued)

(56) References Cited

U.S. PATENT DOCUMENTS 6,234,996 B1 * 5/2001 Bagaoisan ........ A61M 5/31566
604/97.01
8,333,730 B2 12/2012 Matusch
(Continued)

FOREIGN PATENT DOCUMENTS

WO WO 01/72361 A1 10/2001
WO WO 2011/101383 A1 8/2011
(Continued)

OTHER PUBLICATIONS

English translation of International Search Report for the corresponding international application—PCT/EP2015/059714 dated Mar. 8, 2016. (3 pages).

*Primary Examiner* — Kami A Bosworth
(74) *Attorney, Agent, or Firm* — Ronald S. Lombard

(57) ABSTRACT

A disposable injector with a piston actuation ram is mounted in a housing, is loaded by a spring energy accumulator and can be unlocked by a displaceable trigger device. The piston actuation ram can be supported by a tensioning rod mounted in the housing. The trigger device comprises a trigger ring displaceable relative to the housing. The tensioning rod can be supported directly or indirectly by a bearing surface of the trigger ring. The bearing surface encloses an angle of between ten degrees and forty five degrees with the longitudinal direction of the disposable injector. The point of the angle lies offset with respect to the trigger ring in the triggering direction of the disposable injector. A disposable injector with increased trigger reliability is developed.

9 Claims, 6 Drawing Sheets

(58) Field of Classification Search
CPC .. A61M 5/31576–5/31586; A61M 2005/2006;
A61M 2005/2013; A61M 2005/202;
A61M 2005/2026; A61M 2005/206;
A61M 2005/2073; A61M 2005/208;
A61M 2005/2086; A61M 2005/2093
See application file for complete search history.

(56) References Cited

U.S. PATENT DOCUMENTS

| | | | | |
|---|---|---|---|---|
| 2003/0105430 A1* | 6/2003 | Lavi | ............. | A61M 5/2033 |
| | | | | 604/136 |
| 2005/0203466 A1* | 9/2005 | Hommann | ............. | A61M 5/326 |
| | | | | 604/240 |
| 2010/0298780 A1* | 11/2010 | Laiosa | ............. | A61M 5/2033 |
| | | | | 604/198 |
| 2011/0098647 A1* | 4/2011 | Jennings | ............. | A61M 5/3202 |
| | | | | 604/154 |
| 2015/0119812 A1 | 4/2015 | Fabien et al. | | |
| 2016/0279343 A1* | 9/2016 | MacDonald | ............. | A61M 5/3153 |

FOREIGN PATENT DOCUMENTS

| | | |
|---|---|---|
| WO | WO 2012/105898 A1 | 8/2012 |
| WO | WO 2014/154490 A2 | 10/2014 |

\* cited by examiner

DISPOSABLE INJECTOR WITH INCREASED TRIGGERING RELIABILITY

CROSS-REFERENCE TO RELATED APPLICATION

This is a continuation-in-part application of pending international application PCT/EP2015/059714 filed May 4, 2015. The said International application PCT/EP2015/059714 is incorporated herein by reference in its entirety as though fully set forth.

BACKGROUND OF THE INVENTION

The invention relates to a disposable injector having a piston actuation ram which is supported in a housing and which is loaded by means of a resilient energy store and which can be unlocked by means of a displaceable triggering device, wherein the piston actuation ram can be supported by means of a tensile rod which is supported in the housing.

DE 10 2008 063 519 A1 discloses such a disposable injector. The triggering can be prevented by means of friction and/or tilting of the components.

The present invention addresses the problem of increasing the triggering reliability of a disposable injector.

SUMMARY OF THE INVENTION

This problem is solved with the features of the claims. To this end, the triggering device comprises a triggering ring which can be displaced relative to the housing. The tensile rod can be supported directly or indirectly by means of an abutment face of the triggering ring. Furthermore, the abutment face defines with the longitudinal direction of the disposable injector an angle between 10 degrees and 45 degrees, wherein the apex of the angle in the triggering direction of the disposable injector is located offset with respect to the triggering ring.

BRIEF DESCRIPTION OF THE DRAWINGS

Further details of the invention will be appreciated from the claims and the following descriptions of schematically illustrated embodiments.

DETAILED DESCRIPTION OF THE INVENTION

Figure 1:
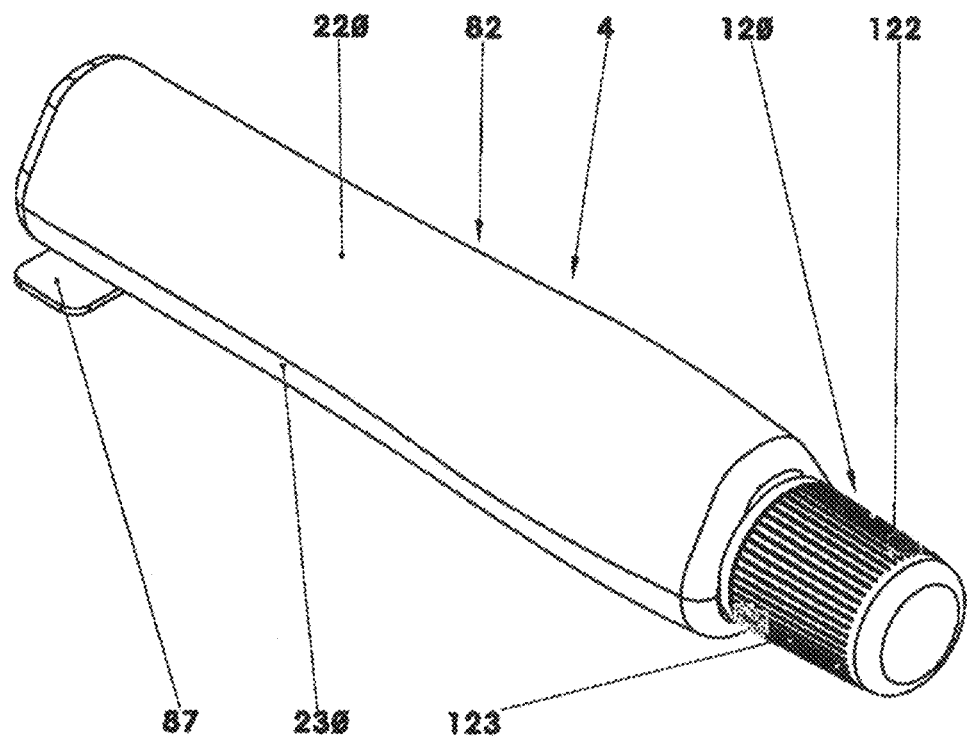
FIG. 1: shows a single-use injector with closure cap.

FIGS. 1-14 show a single-use or disposable injector (4). Such injectors (4) are used for the one-off introduction of an injection solution (1) or a solvent which is stored in a cylinder/piston unit (100) into the skin of a patient.

The disposable injector (4) comprises a covering housing (82) in which an inner housing (10) having a piston actuation ram (60) and a helical compression spring (50) as a permanently loaded resilient energy store (50) and a cylinder/piston unit (100) are arranged. The cylinder/piston unit (100) is closed by means of a protective cap (120). The triggering of the single-use injector (4) is prevented by means of a securing sliding member (87). This member may be removable for unlocking or it may be displaceable in a manner guided in the single-use injector (4). The housing (10) and the covering housing (82) are, for example, produced from plastics material. This may be a thermoplastic or thermosetting material, for example, POM, ABS, etcetera.

The covering housing (82) comprises in the embodiment an upper shell (220) and a lower shell (230). The two shells (220, 230) are connected to each other by means of journal connections (228, 238) and, for example, secured in a positive-locking and/or materially engaging manner. The upper shell (220) and the lower shell (230) may, for example, be adhesively bonded, welded to each other, etc. The upper shell (220) and the lower shell (230) may also be engaged with each other.

Figure 5:
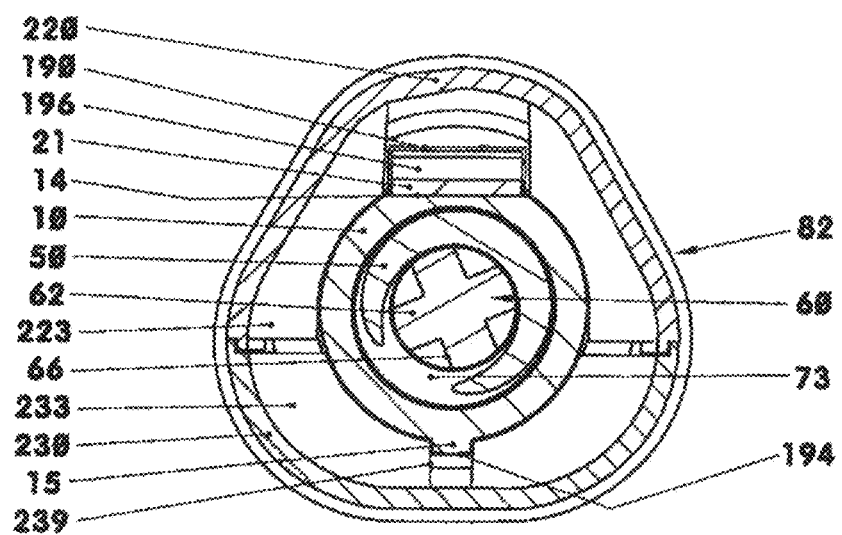
FIG. 5: is a cross-section of the single-use injector above the triggering ring.

The covering housing (82) which is polygonal in cross-section has in the embodiment an at least substantially regular, triangle-like cross-section, cf. FIG. 5. The cross-sectional surface-area in the rear region of the disposable injector (4) facing away from the injection location is 70% of the cross-sectional surface-area in the front region of the disposable injector (4) facing the injection location. The constant increase of the cross-sectional surface-area is located, when viewed from the operator, in the third quarter of the length of the disposable injector (4).

Figure 4:
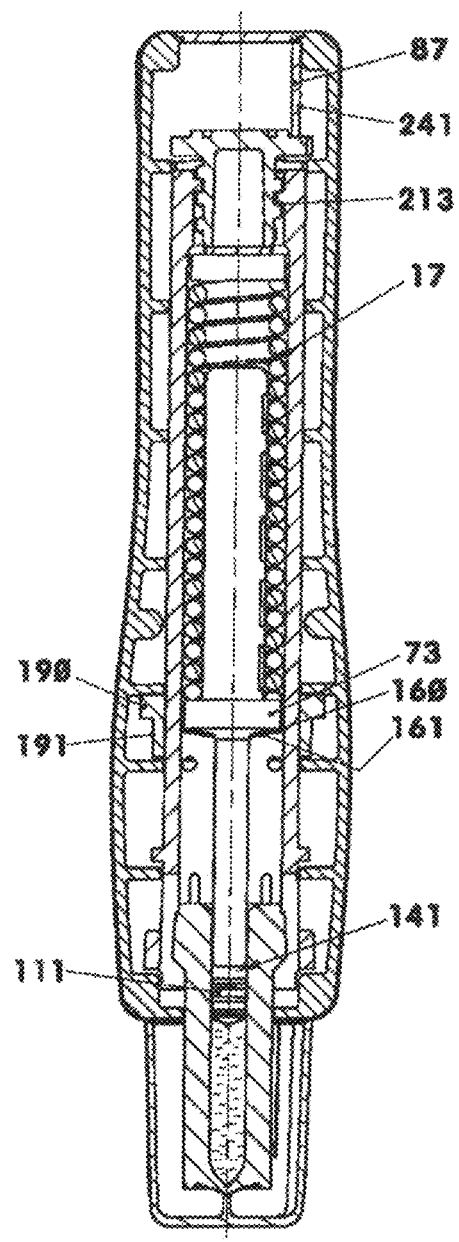
FIG. 4: is a longitudinal section which is normal with respect to FIG. 3.
Figure 3:
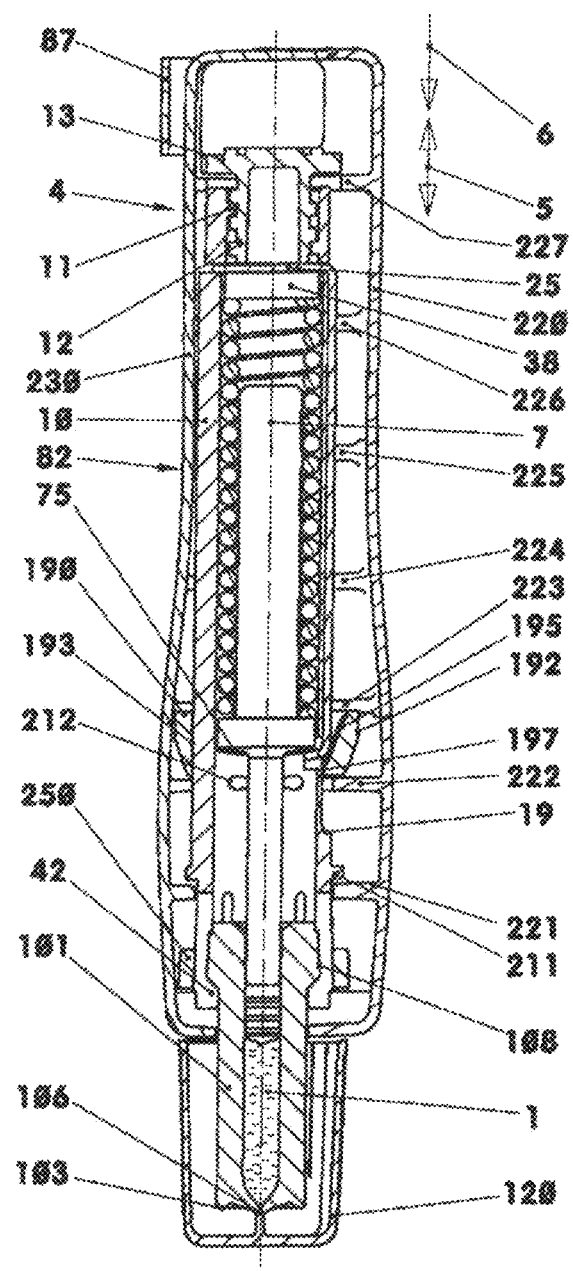
FIG. 3: is a longitudinal section of the single-use injector from FIG. 1.

The disposable injector (4) comprises a tubular housing (10) in which a resilient energy store (50) and a piston actuation ram (60) are arranged. In the front region facing the injection location, the housing (10) has inwardly protruding resilient hooks (42). In the illustrations of FIGS. 3 and 4, the, for example, prefilled, cylinder/piston unit (100) is inserted and engaged in the resilient hooks (42).

The housing (10) has a substantially cylindrical inner contour. An inner thread (11) is arranged in the rear region facing away from the injection location. A support screw (12) having a hexagonal portion (13) is located therein. The outer contour of the housing (10) has a cylindrical basic shape with a flattened portion (14), cf. FIG. 2. In the region of the flattened portion (14), a support rod (21) is in abutment with the housing (10). The support rod (21) protrudes with a clamping member (25) into an upper slot (16) of the housing (10). A wrap-around hook (26) of the support rod (21) protrudes through a lower opening (18) with a rectangular cross-sectional surface-area (18) into the housing (10). With respect to the flattened portion (14), the housing (10) has a guiding rib (15) which is orientated in the longitudinal direction (5) of the disposable injector (4), cf. FIGS. 5 and 8.

The piston actuation ram (60) comprises a, for example, cylindrical guiding journal (62), a ram plate (73) and a piston sliding member (76). The guiding journal (62) carries and guides the resilient energy store (50) which is constructed in this instance as a helical compression spring (50).

The upper end of the helical compression spring (50) in FIGS. 3 and 4 is supported by means of a disk (38) and the clamping member (25) of the support rod (21) on the support screw (12). The guiding journal (62) has circle-segment-like recesses (66) which are orientated in a radial direction. The disposable injector (4) may also be constructed without the support disk (38).

The ram plate (73) of the piston actuation ram (60) is constructed in a disk-like manner and orientated normally with respect to the longitudinal center axis (7) of the disposable injector (4). It has a collar face (75) which faces away from the helical compression spring (50) and which is constructed in a conical manner. The apex angle of the notional cone of the collar face (75) is, for example, 160 degrees.

Figures 6, 7:
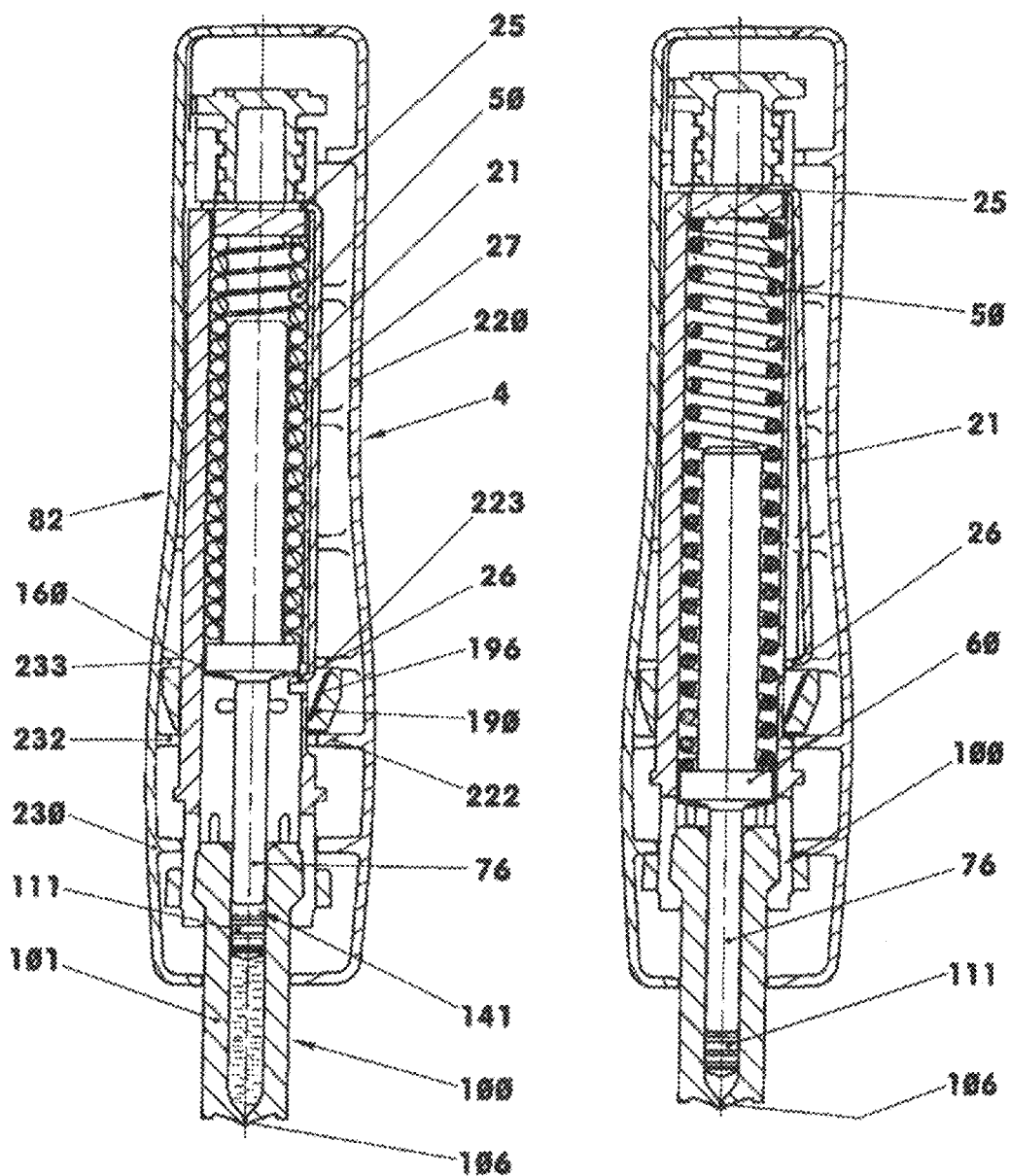
FIG. 6: shows a single-use injector after the triggering.
FIG. 7: shows a single-use injector with an emptied cylinder/piston unit.
Figure 8:
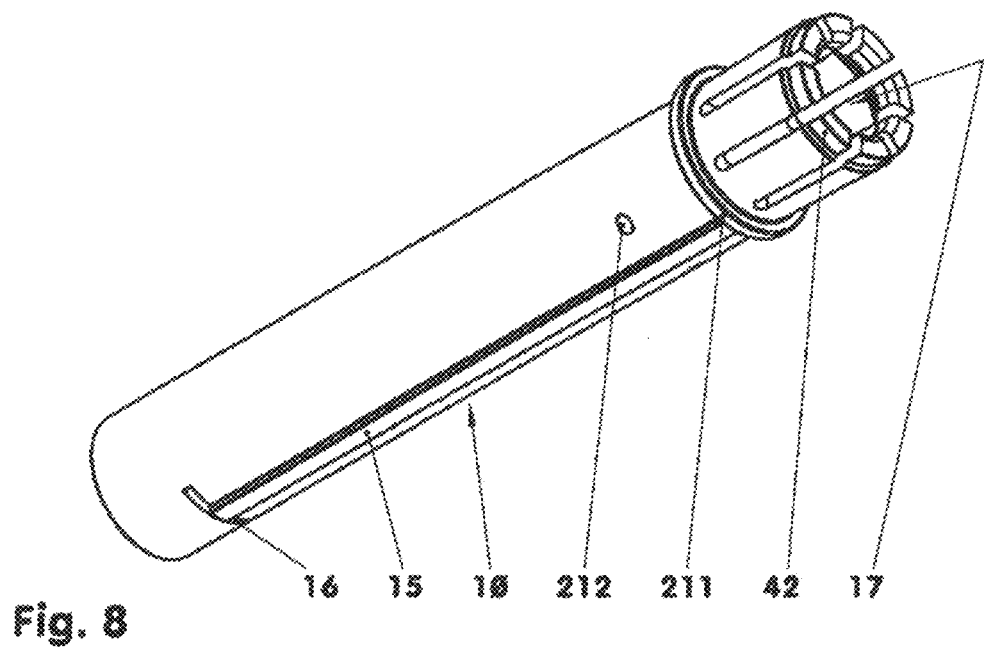
FIG. 8: is a dimetric view of the housing.
Figure 9:
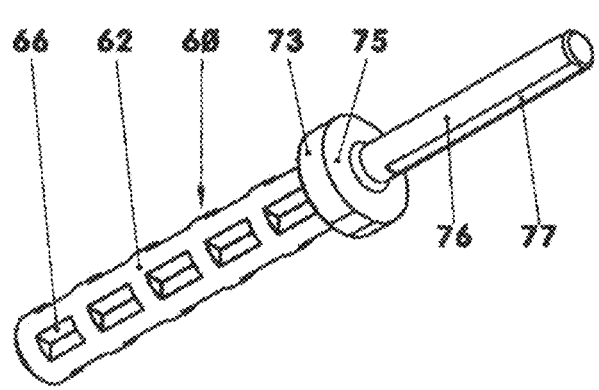
FIG. 9: is a dimetric view of the piston actuation ram.
Figure 10:
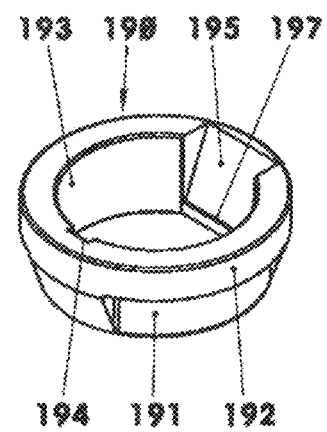
FIG. 10: is a dimetric view of the triggering ring.
Figure 11:
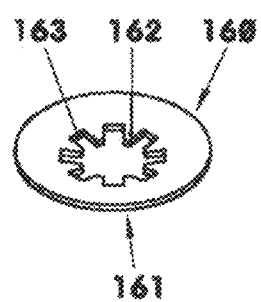
FIG. 11: is a dimetric illustration of the support disk.

A support disk (160) is in abutment with this collar face (75), cf. FIG. 11. In the embodiment, the support disk (160) is a perforated disk and has grooves (163) and wedges (162) which are arranged around the central hole and by means of which it is located in a positive-locking manner on the piston sliding member (76) of the piston actuation ram (60). The support disk (160) is constructed in a frustoconical manner as a side view. It is, for example, produced from a metal material, for example, an austenitic, corrosion-resistant steel. In the illustration of FIG. 6, it is fixed in its position by means of the wrap-around hook (26) of the support rod (21).

The rod-like piston sliding member (76) has in the embodiment an at least substantially cylindrical structure. For example, it has key flats (77) which are orientated in the longitudinal direction of the single-use injector (4). Along these key flats (77), air can escape more rapidly when the piston sliding member (76) is introduced into the cylinder/piston unit (100).

Figure 2:
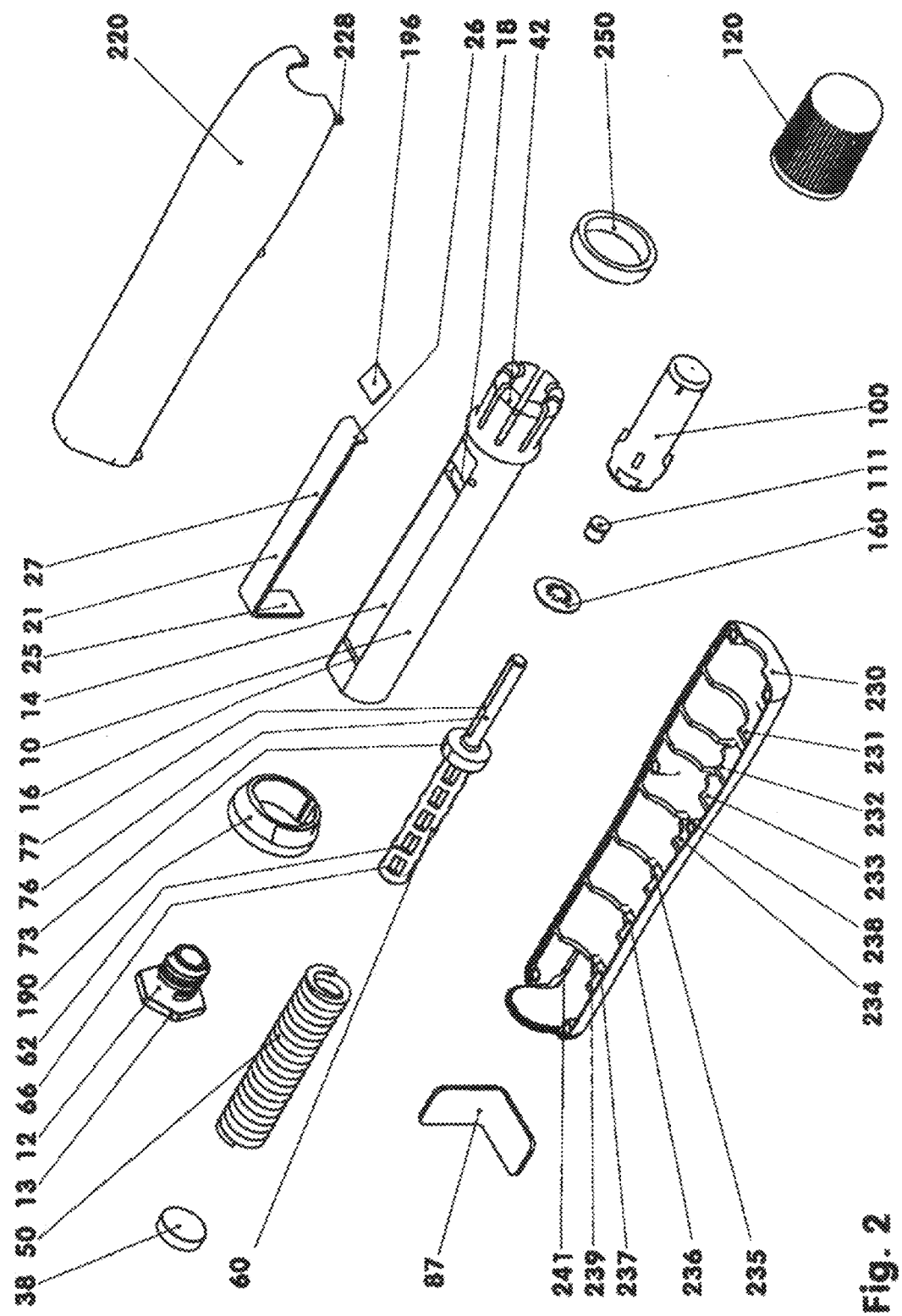
FIG. 2: is an exploded drawing of the single-use injector of FIG. 1.
Figure 12:
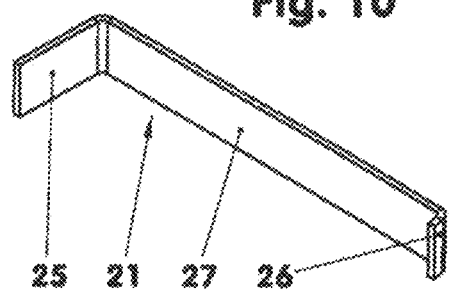
FIG. 12: is a dimetric illustration of the support rod.
Figure 13:
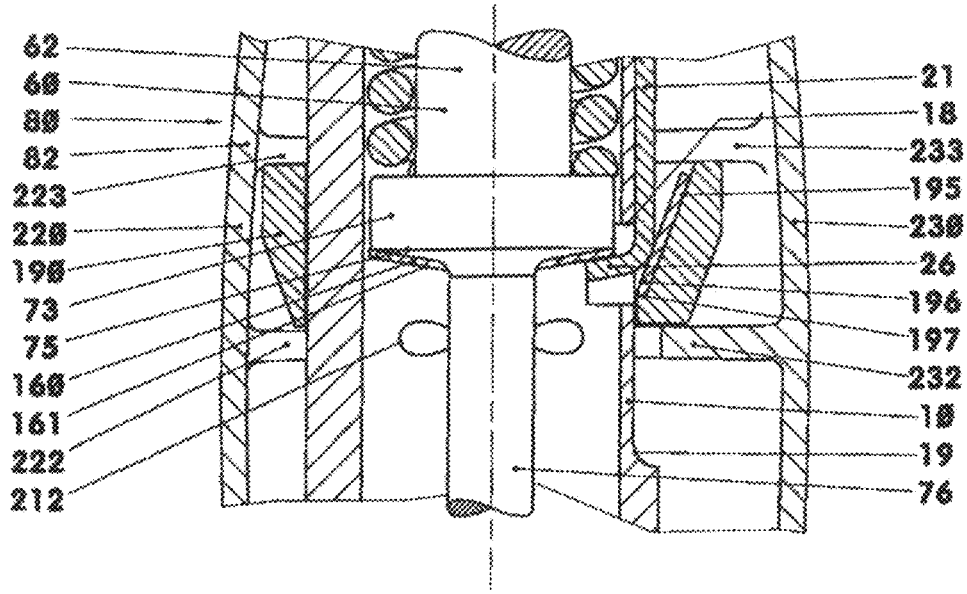
FIG. 13: shows a detail of the triggering device before the triggering.

The support rod (21), cf. FIGS. 2, 3 and 12, is produced from a sheet metal strip, with, for example, a constant rectangular cross-sectional surface-area. The width of the support rod (21) in a direction normal relative to the longitudinal direction (5) of the single-use injector (4) is in the embodiment eight times greater than the thickness thereof. The material of the support rod (21) is an austenitic spring steel The elasticity modulus thereof is, for example, greater than 190,000 Newton per square millimeter. The support rod (21) comprises a main member (27), the clamping member (25) and the wrap-around hook (26). In the illustration of FIG. 3, the main member (27) is parallel with the flattened portion (14). The length thereof is, for example, seven times the width of the support rod (21). The rear end of the support rod (21) illustrated at the top in FIG. 3 faces in the direction of the inner space (17) of the disposable injector (4) and forms the clamping member (25). The clamping member (25) which is, for example, bent by means of a bending shaping method forms with the main member (27) an angle of, for example, 92 degrees.

The front lower end of the support rod (21) in FIG. 3 also faces in the direction of the inner space (17) and forms the wrap-around hook (26). The wrap-around hook (26) defines with the main member (27) an angle which is greater, by the inclination angle of the collar face (75) with respect to a normal plane of the longitudinal center axis (7) of the single-use injector (4), than a right angle. The length of the wrap-around hook (26) is, for example, 20% of the length of the clamping member (25).

The cylinder/piston unit (100) comprises a, for example, transparent cylinder (101) and a piston (111) which is guided in the cylinder (101). In the illustrations of FIGS. 3, 4 and 6, the piston (111) is located in a rear position. Between the piston (111) and the piston sliding member (76) which is also guided in the cylinder (101) there is an intermediate space (141). The length thereof is in the embodiment two millimeters. This length may be between one millimeter and ten millimeters.

The outlet opening (106) of the cylinder/piston unit (100) located at the bottom in FIGS. 3, 4, 6 and 7 is constructed as a short, cylindrical nozzle-like hole (106).

In the illustrations of FIGS. 3, 4, 6 and 7, the cylinder/piston unit (100) is inserted into the housing (10). The resilient hooks (42) engage behind the upper collar (108) of the cylinder/piston unit (100). A securing ring (250) rests on the resilient hook (42)—below the plane of the lower end of the collar (108). This securing ring (250) has in the embodiment a circular base face. The inner diameter thereof is, for example, greater than the outer diameter of the housing (10) in the region of the non-deformed resilient hook (42). The outer diameter is, for example, greater than the inner diameter of the covering housing (82) and smaller than the outer diameter of the closure cap (120).

A triggering ring (190) is located on the housing (10). It is illustrated as a single component in FIG. 10. The covering face thereof has an upper cylindrical portion (192) and a lower portion (191). The lower portion (191) is constructed to be partially cylindrical and partially frustoconical. The inner wall (193) which is cylindrical in terms of the basic shape has at one side a rotation prevention groove (194) which is orientated in the longitudinal direction (5) of the disposable injector (4). At the opposite side, an oblique abutment face (195) is formed. This abutment face (195) is, for example, orientated at an angle of 20 degrees with respect to the longitudinal direction (5) of the single-use injector (4). This angle whose tip is located in the triggering direction (6) of the disposable injector (4) in a state offset with respect to the triggering ring (190) may be between 10 degrees and 45 degrees. The abutment face (195) terminates at a lower shoulder (197). In the region of this lower shoulder (197), the inner wall is delimited by a chord of the basic shape.

In the embodiment, a metal insertion sheet (196) which is constructed as a sliding plate (196) is located on the abutment face (195). However, the disposable injector (4) may also be constructed without the metal insertion sheet (196). The metal insertion sheet (196) comprises, for example, a corrosion-resistant austenitic steel. The elasticity modulus of this material is greater than 190,000 Newton per square millimeter. The sliding plate (196) is positioned on the shoulder (197). Before the single-use injector (4) is triggered, cf. FIGS. 3 and 13, the support rod (21) is supported on the sliding plate (196). It is consequently indirectly supported on the abutment face (195). The static friction coefficient of this material combination is, for example, less than 0.2. Even with long-term storage, the pressure-loaded support rod (21) does not bring about any deformations of the sliding plate (196). Consequently, even after a relatively long period of storage, reliable triggering is ensured.

The two shells (220, 230) of the triggering sleeve (82) have at the inner side thereof in each case reinforcement ribs (221-227; 231-237). These transverse ribs (221-227; 231-237) are orientated normally with respect to the longitudinal direction (5) of the single-use injector (4). In this instance, the rear reinforcement ribs (223-227; 232-237) each have two portions, between which a groove (239) is arranged. The foremost reinforcement ribs (221, 222; 231) facing away from the operator are each constructed in an interruption-free manner. The upper shell (220) and the lower shell (230) are connected to each other by means of a plurality of journal connections (228, 238). In this instance, in the embodiment the upper shell (220) has at the separation joint six journals (228) which engage in journal holes (238) of the lower shell (230). Where applicable, the journal connections (228, 238) may engage with each other during the assembly. Adhesive bonding of the lower shell (230) to the upper shell (220) is also conceivable.

During assembly of the single-use injector (4), for example, the support disk (160) is first pushed onto the piston sliding member (76) of the piston actuation ram (60). The helical spring (50) is placed on the guiding journal (62) of the piston actuation ram (60). The triggering ring (190) is, in a state guided on the flattened portion (14) and on the guiding rib (15), fitted onto the housing (10) from the rear until it is located below the rectangular recess (18). For example, the sliding plate (196) may already be placed and fixed in the triggering ring (190). An annular housing expansion (19) prevents the further movement or displacement of the triggering ring (190) downward. After the clamping member (25) of the support rod (21) has been inserted into the upper housing slot (16), the disk (38) is inserted from below into the housing (10). The thickness of the disk (38) may be selected in accordance with the required resilient pretensioning. Accordingly, the preassembled components (50, 60, 160) are also inserted from below into the housing (10) so that the helical compression spring (50) is in abutment with the pressure disk (38) and it contacts the clamping member (25).

The support screw (12) can now be screwed in until it is in abutment with the clamping member (25) or presses against it. Where applicable, the thread pitch (213) of the support screw (12) and/or the housing (10) may have a planar tooth arrangement in order to prevent unintentional release of the support screw (12). The piston actuation ram (60) is pressed in, for example, by means of a tool. In this instance, the helical compression spring (50) is tensioned. For example, the housing (10) is retained in this instance on a retention ring (211). The wrap-around hook (26) of the support rod (21) is introduced into the rectangular recess (18) and placed at the lower side (161) of the support disk (160). The triggering ring (190) is pulled upward until it is in abutment with the support rod (21). The support rod (21) is now supported on the sliding plate (196), cf. FIG. 13. In order to secure the assembly position, a, for example, U-shaped curved member may be introduced into assembly openings (212) of the housing (10). This curved member secures the position of the triggering ring (190) after the clamping device of the resilient energy store (50) has been removed. This preassembly group may now, for example, be conveyed to another workplace. There is no risk of unintentional triggering.

In the lower region of the single-use injector (4), the securing ring (250) is pushed onto the resilient hook (42) until it is, for example, in abutment with the retention ring (211). Now, for example, the pre-filled cylinder/piston unit (100) can be inserted into the housing (10) and engaged therein. The securing ring (250) is pulled forward and thus fixes the position of the cylinder/piston unit (100).

The preassembly group with the housing (10) and the cylinder/piston unit (100) can now be conveyed further or processed.

During the final assembly, this preassembly group is, for example, inserted into the lower shell (230). In this instance, the rib (15) of the housing (10) is centered in the longitudinal groove (239) of the lower shell (230). The triggering ring (190) is located between the second transverse ribs (222, 232) and the third transverse ribs (223, 233). The head of the support screw (12) protrudes beyond the rearmost transverse rib (227; 237). The closure cap (120) is located outside the covering housing (82). The securing element (87) is introduced into the slot (241) of the lower shell (230) and, for example, clamped between the support screw (12) and the housing (82). The support screw (12) can be secured against further rotation, for example, in a positive-locking manner. Where applicable, an additional compression spring between the support screw (12) and the sleeve (82) may increase the resistance against unintentional triggering. This spring also determines the resistance of the disposable injector (4) during triggering. The U-shaped curved member may be removed.

At the end of the assembly, the upper shell (220) is placed on the lower shell (230) and secured, for example, by means of adhesive bonding, engagement, etcetera. Now an additional originality closure, for example, a banderole, may be fitted over the covering housing (82) and the closure cap (120). On the peripheral face (122) thereof, it has a fluting (123) in order to prevent fingers from sliding off.

It is also conceivable to carry out the assembly in a different sequence from the one described.

The fully assembled disposable injector (4) may now be packaged and marketed. If, for example, it is placed on a table after unpacking, as a result of the housing geometry there is no risk of it rolling away.

Before the single-use injector (4) is used, the originality closure is first removed. After the closure cap (120) has been removed, the securing element (87) can be pulled out. The single-use injector (4) is now ready for use and is, for example, placed on the skin of the patient. For example, the end face (103) of the cylinder/piston unit (100) bonds to the skin of the patient. In this state, the self-locking between the support rod (21) and the triggering ring (190) also prevents unintentional self-triggering of the disposable injector (4), cf. FIG. 13.

In order to trigger the single-use injector (4), the covering housing (82) which forms a triggering sleeve (82), is displaced forward in the triggering direction (6), that is to say, in the direction of the skin of the patient. The triggering sleeve (80) displaces in this instance the triggering ring (190) relative to the housing (10) in a downward direction in the sectioned illustrations of FIGS. 3, 4, 6 and 7. In FIG. 6, the non-static state is illustrated directly after triggering. The resilient energy store (50) presses the ram plate (73) forward. In this instance, the pressure disk (160) displaces the wrap-around hook (26) of the support rod (21). The support rod (21) slides outward along the sliding plate (196) and consequently completely releases the piston actuation ram (60). In this instance, the support rod (21) may optionally strike an insulating rubber layer. The piston actuation ram (60), in a state loaded by the resilient energy store (50) which is becoming relaxed, moves rapidly forward or downward. The piston sliding member (76) strikes the piston (111) and pushes it forward. In this instance, the air is displaced from the intermediate space (141) along the key flats (77). The injection solution (1) which is stored in the cylinder (101) is displaced through the outlet opening (106) and the hard skin of the patient into the body of the patient.

Figure 14:
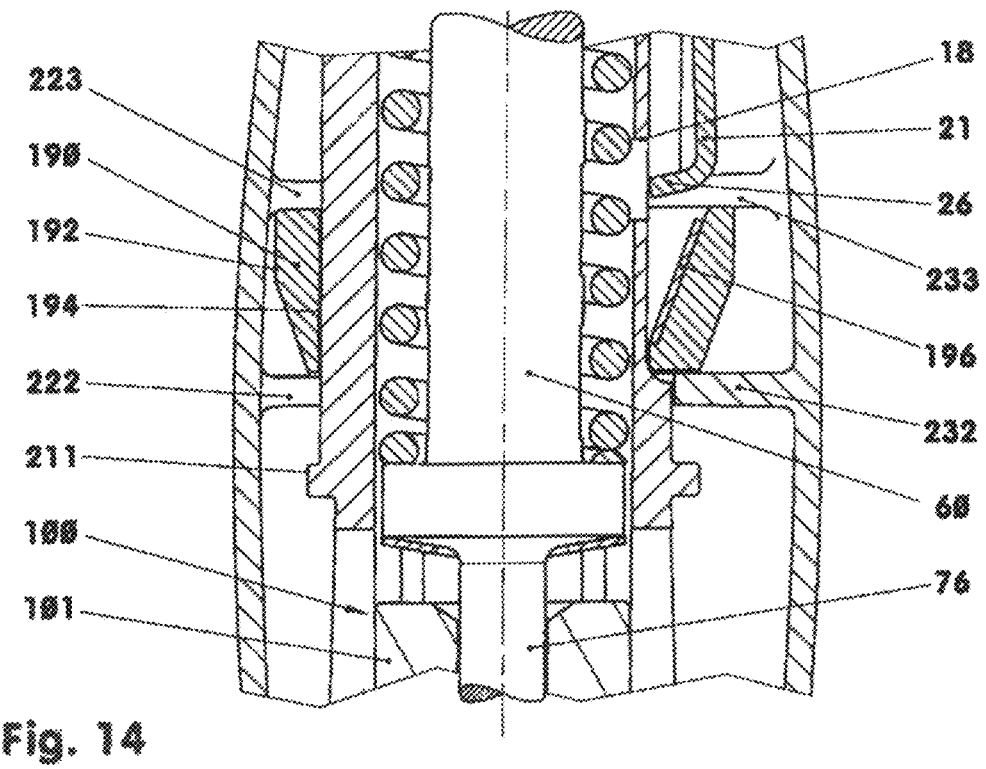
FIG. 14: shows a detail of the triggering device after the triggering.

FIGS. 7 and 14 show the single-use injector (4) after the triggering. The triggering ring (190) is displaced downward relative to the housing (10). The support rod (21) is displaced outward. In this instance, it blocks, for example the triggering sleeve (82) with the triggering ring (190) against being pushed in again. The resilient energy store (50) is relaxed. The piston actuation ram (60) is located in the front end position thereof. The cylinder/piston unit (100) is emptied.

Of course, it is also conceivable to combine the different embodiments mentioned with each other.

LIST OF REFERENCE SIGNS

1 Injection solution, water for injection purposes
4 Single-use injector, disposable injector
5 Longitudinal direction
6 Triggering direction
7 Longitudinal center axis
10 Housing
11 Inner thread
12 Support screw
13 Hexagonal portion
14 Flattened portion
15 Guiding rib
16 Housing opening, slot-like
17 Inner space
18 Housing opening with rectangular cross-section
19 Housing expansion
21 Support rod, locking rod
25 Clamping member
26 Wrap-around hook
27 Main member
38 Disk
42 Resilient hook
50 Resilient energy store, helical compression spring, spring
60 Piston actuation ram
62 Guiding journal
66 Recesses
73 Ram plate
75 Collar face
76 Piston sliding member
77 Key flats
80 Triggering unit
82 Triggering element, triggering sleeve
87 Securing sliding member, securing element
100 Cylinder/piston unit
101 Cylinder
103 End face
106 Hole/discharge opening
108 Collar
111 Piston
120 Closure cap
122 Peripheral face
123 Fluting
141 Intermediate space
160 Support disk, pressure disk
161 Lower side
162 Wedges
163 Grooves
190 Triggering ring
191 Lower region
192 Cylindrical region
193 Inner wall
194 Rotation prevention groove
195 Abutment face
196 Metal insertion sheet, sliding plate
197 Shoulder
211 Retention ring
212 Assembly openings
213 Thread pitch
220 Upper shell
221, 222 Reinforcement ribs, transverse ribs, one-piece
223-227 Reinforcement ribs, transverse ribs, two-piece
228 Journal
230 Lower shell
231 Reinforcement rib, transverse rib, one-piece
232-237 Reinforcement rib, transverse rib two-piece
238 Journal holes
239 Longitudinal groove
241 Slot
250 Securing ring

What is claimed is:

1. A disposable injector (4) having a longitudinal center axis (7) and having a piston actuation ram (60) which is supported in an inner tubular a housing (10) and which is loaded by a resilient energy store (50) comprising a helical compression spring and which can be unlocked by a displaceable triggering device (80), characterized in that the piston actuation ram (60) including an elongated cylindrical guiding journal (62) configured in an operative position to axially extend through and carry the helical compression spring (50), a disk-like ram plate (73) configured to retain the helical compression spring (50) on the elongated cylindrical guiding journal (62) operatively attached to the disk-like ram plate (73), a rod-like piston sliding member (76) operatively configured to operatively engage a cylinder/piston unit (100), a tensile locking rod (21) configured to support the piston actuation ram (60), the tensile locking rod (21) having a U-shape and consisting of a straight main member (27) and an integral clamping member (25) at one end of the straight main member (27) extending perpendicularly to the straight main member (27) and an integral wrap-around hook (26) at another end of the straight main member (27) having a predetermined curvature extending from the straight main member (27), the inner tubular housing (10) having a cylindrical basic shape and including an exterior surface elongated flattened portion (14) of predetermined length having a first slot-like aperture (16) proximate one end of the exterior surface elongated flattened portion (14) and a second slot-like aperture (18) proximate another end of the exterior surface elongated flatted portion (14), the straight main member (27) in the operative position configured to be carried on the exterior surface elongated flattened portion (14), the clamping member (25) configured in the operative position to pass through the first slot-like aperture (16) for clamping an end of the helical compression spring (50), the wrap-around hook (26) configured in the operative position to pass through the second slot-like aperture (18) and configured to grasp the disk like ram plate (73) to lock the piston actuation ram (60) and to lock the helical compression spring (50) in a compressed state prior to triggering of the disposable injector (4) and configured upon triggering by the displaceable triggering device (80) to expand outwardly away from the longitudinal center axis (7) and away from the second slot-like aperture (18), the displaceable triggering device (80) comprising a triggering sleeve covering housing (82) which can be displaced relative to the inner tubular housing (10), a displaceable triggering ring (190) displaceably arranged on the inner tubular housing (10) and supported by the triggering sleeve covering housing (82), the displaceable trigger ring (190) having a cylindrical inner wall (193) having an oblique abutment face (195) terminating at a lower shoulder (197) of the displaceable triggering ring (190), the oblique abutment face (195) facing inwardly and configured to retain and compress the wrap around hook (26) of the tensile locking rod (21) in the operative position in the slot-like aperture (18) to lock the ram (60) prior to an actuation of the triggering sleeve covering housing (82), the triggering sleeve covering housing (82), upon actuation of the triggering sleeve covering housing (82), configured to displace the displaceable triggering ring (190) longitudinally relative to the inner housing (10) and to simultaneously cause the tensile locking rod (21) in cooperation with the oblique abutment face (195) to slide outwardly and to release the compressed wrap-around hook (26), the grasped disk-like plate (73) and the helical compression spring (50), the inwardly facing oblique abutment face (195) of the triggering ring (190) defines, with a longitudinal direction (5) of the disposable injector (4), a predetermined angle, wherein the apex of the predetermined angle is in a triggering direction (6) of the disposable injector (4) and is located offset with respect to the triggering ring (190).

2. The disposable injector (4) as claimed in claim 1, characterized in that the triggering ring (190) and the inner tubular housing (10) are constructed so as to be rotationally secure with respect to each other.

3. The disposable injector (4) as claimed in claim 1, characterized in that the oblique abutment face (195) carries a sliding plate (196).

4. The disposable injector (4) as claimed in claim 1, characterized in that the tensile locking rod (21) is constructed as a single sheet metal strip.

5. The disposable injector (4) as claimed in claim 4, characterized in that the tensile locking rod (21) comprises austenitic spring steel with a predetermined elasticity modulus.

6. The disposable injector (4) as claimed in claim 5, characterized in that the predetermined elasticity modulus is greater than 190,000 Newton per square millimeter.

7. The disposable injector (4) as claimed in claim 1, characterized in that the clamping member (25) is fixed in the inner tubular housing (10) by a support screw (12) which is secured in the inner tubular housing (10).

8. The disposable injector (4) as claimed in claim 1, characterized in that a relative movement between the displaceable triggering device (80) and the inner tubular housing (10) can be blocked by a releasable or unlockable securing element (87).

9. The disposable injector (4) as claimed in claim 1, characterized in that the predetermined angle is between 10 degrees and 45 degrees.

* * * * *